US00PP37127P2

(12) United States Plant Patent
Bourne

(10) Patent No.: US PP37,127 P2
(45) Date of Patent: Dec. 9, 2025

(54) GRAPEVINE PLANT NAMED 'SV36-47-269'

(50) Latin Name: *Vitis vinifera*
Varietal Denomination: SV36-47-269

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 18/831,547

(22) Filed: Apr. 14, 2025

(51) Int. Cl.
*A01H 6/88* (2018.01)
*A01H 5/08* (2018.01)

(52) U.S. Cl.
USPC ..... Plt./207

(58) Field of Classification Search
USPC ..... Plt./207
CPC ..... A01H 6/88; A01H 5/08
See application file for complete search history.

*Primary Examiner* — Keith O. Robinson
(74) *Attorney, Agent, or Firm* — Eric C. Cole; Baker Manock & Jensen, PC

(57) ABSTRACT

A new and distinct variety of grapevine plant named 'SV36-47-269' particularly characterized by its large, yellow-green, crisp, sweet berries with light muscat flavor. The vines are very responsive to exogenous gibberellic acid application and trunk girdling and produce berries which are about 25% larger than natural size. Vines are fruitful when spur pruned to two buds per cane with new shoots producing mostly two clusters per shoot.

6 Drawing Sheets

Latin name of the genus and species of the plant claimed: The plant claimed relates to a new and distinct variety of *Vitis vinifera*.

Variety denomination: The plant claimed shall be known as 'SV36-47-269'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV36-47-269'. As used herein, 'grapevine' refers to all plant parts including vines, shoots, canes, tendrils, leaves, fruit and roots of 'SV36-47-269'. This new cultivar originated from a cross conducted in May 2014 near McFarland, California, between female parent grapevine selection 'SV30-23-590' (unpatented) and male parent grapevine cultivar 'SV21-66-226' (U.S. Plant Pat. No. 24,531). Resultant ovules from the cross were harvested 42 days after pollination and cultured on McCown's Wood Plant Medium. Subsequently, the resultant embryonic plants were extracted from those ovules and were cultured in the same medium in the laboratory under twelve hours of light from standard fluorescent lamps at 27° C. The seedlings from this effort were transplanted to the greenhouse in November of 2015 and grown at 27° C. with 12 hours illumination under high pressure sodium vapor lamps. The seedling population of 567 seedlings was planted in the field in the spring of 2016 near Delano, California. The new grapevine was selected from this seedling population on Sep. 21, 2018. It was then propagated by cuttings and was bench grafted to 'Freedom' (unpatented) rootstock near McFarland, California in 2019. The present invention has been found to retain its distinctive characteristics through two successive asexual propagations.

Grapevine 'SV36-47-269' differs from its female parent grapevine 'SV30-23-590' (unpatented) by having ovate berries which are very crisp while grapevine 'SV30-23-590' has berries which are spherical and slightly soft in texture.

Grapevine 'SV36-47-269' differs from its male parent 'SV21-66-226' (U.S. Plant Pat. No. 24,531) in that 'SV36-47-269' has natural berries averaging almost 7 grams while 'SV21-66-226' has natural berries averaging about 4 grams.

Grapevine 'SV36-47-269' is most similar to commercially available 'Autumn King' (U.S. Plant Pat. No. 16,284) but differs from it in that the clusters of 'SV36-47-269' has fruit with pleasant, non-herbaceous muscat flavor and ovate shaped berries while 'Autumn King' has berries which are elliptic in shape and which have herbaceous flavor.

SUMMARY OF THE INVENTION

The following are the most outstanding and distinguishing characteristics of the ripe fruit of this new variety when grown under normal horticultural practices near McFarland, California:

a. Fruit clusters with large, sweet, yellow green berries with crisp texture and muscat flavor.
b. Berries which are very responsive to applications of exogenous gibberellic acid which along with trunk girdling increase the natural berry size by about twenty five percent.

BRIEF DESCRIPTION OF THE DRAWINGS

This new grapevine is illustrated by the accompanying photographs which show fruit clusters, leaves, canes and tendrils. The colors shown are as true as can be reasonably obtained by conventional photographic procedures. The photographs were taken from the original seedling vine in 2018. The remainder of the photographs were taken from a vine grafted to 'Freedom' rootstock in 2024.

DETAILED BOTANICAL DESCRIPTION

Figure 1:
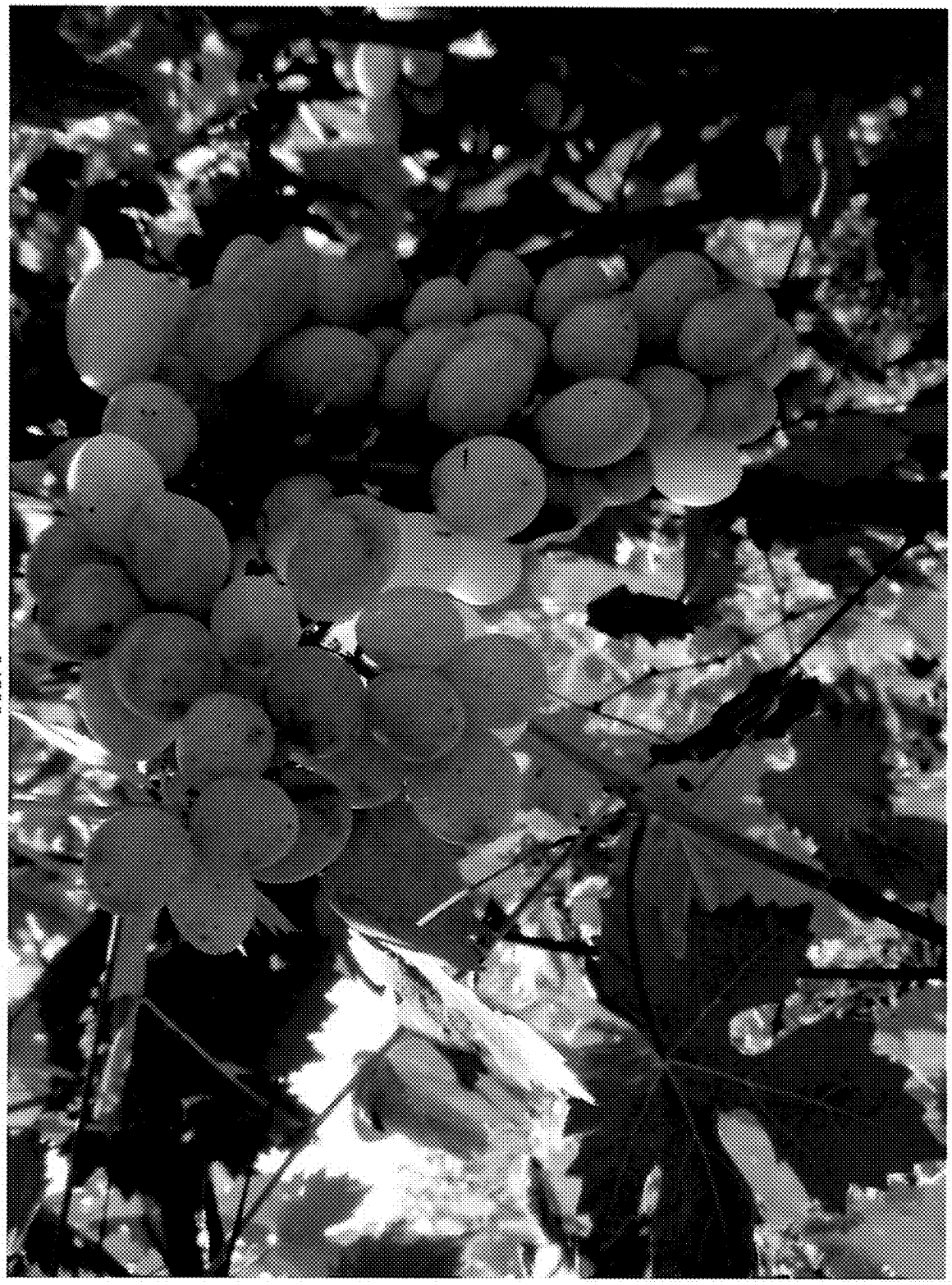
FIG. 1 Fruit cluster on the seedling vine taken in September 2018.
Figure 2:
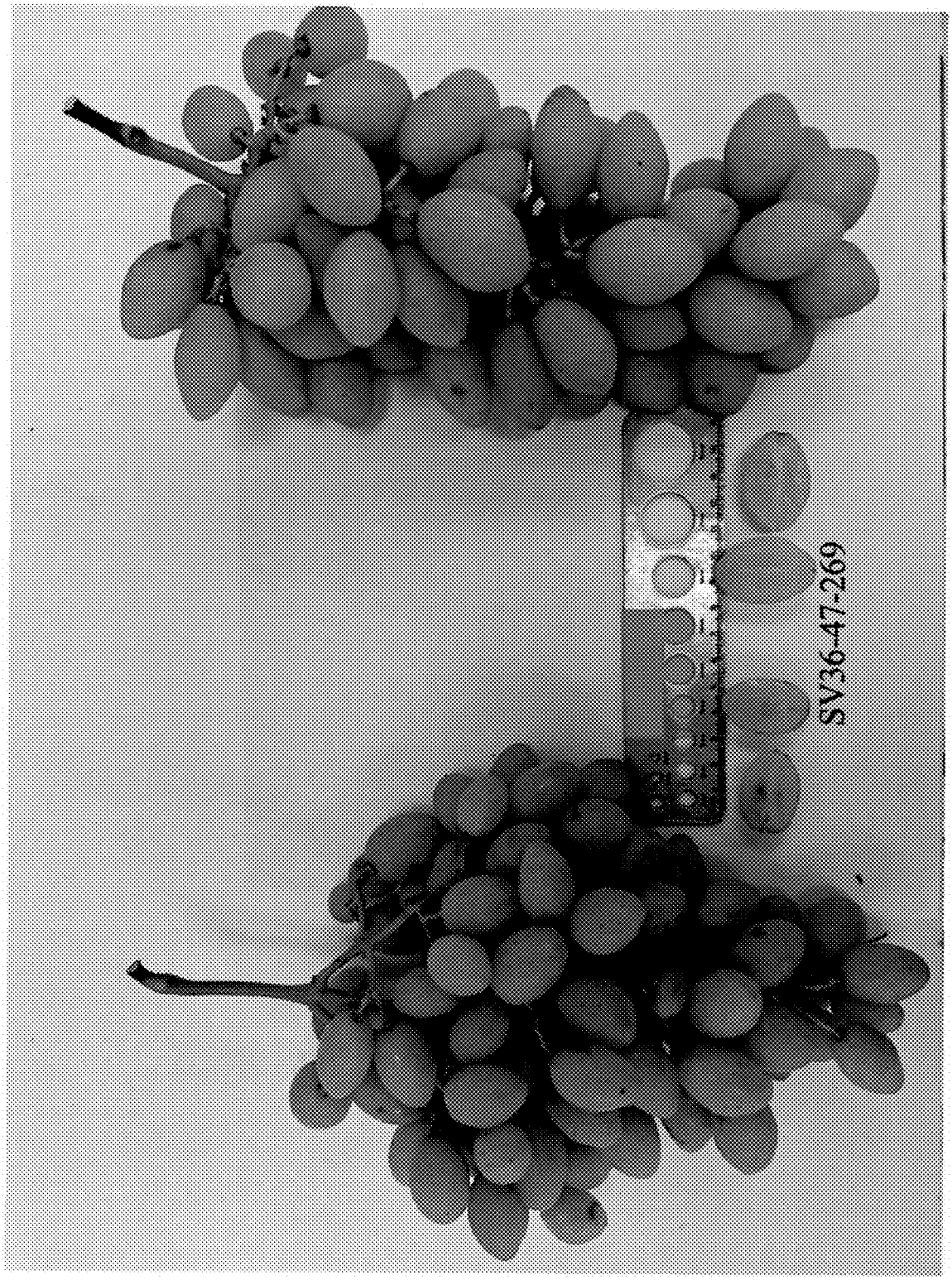
FIG. 2 Fruit clusters from control vine with natural fruit on left and fruit from a vine treated with gibberellic acid and trunk girdling on right.
Figure 3:
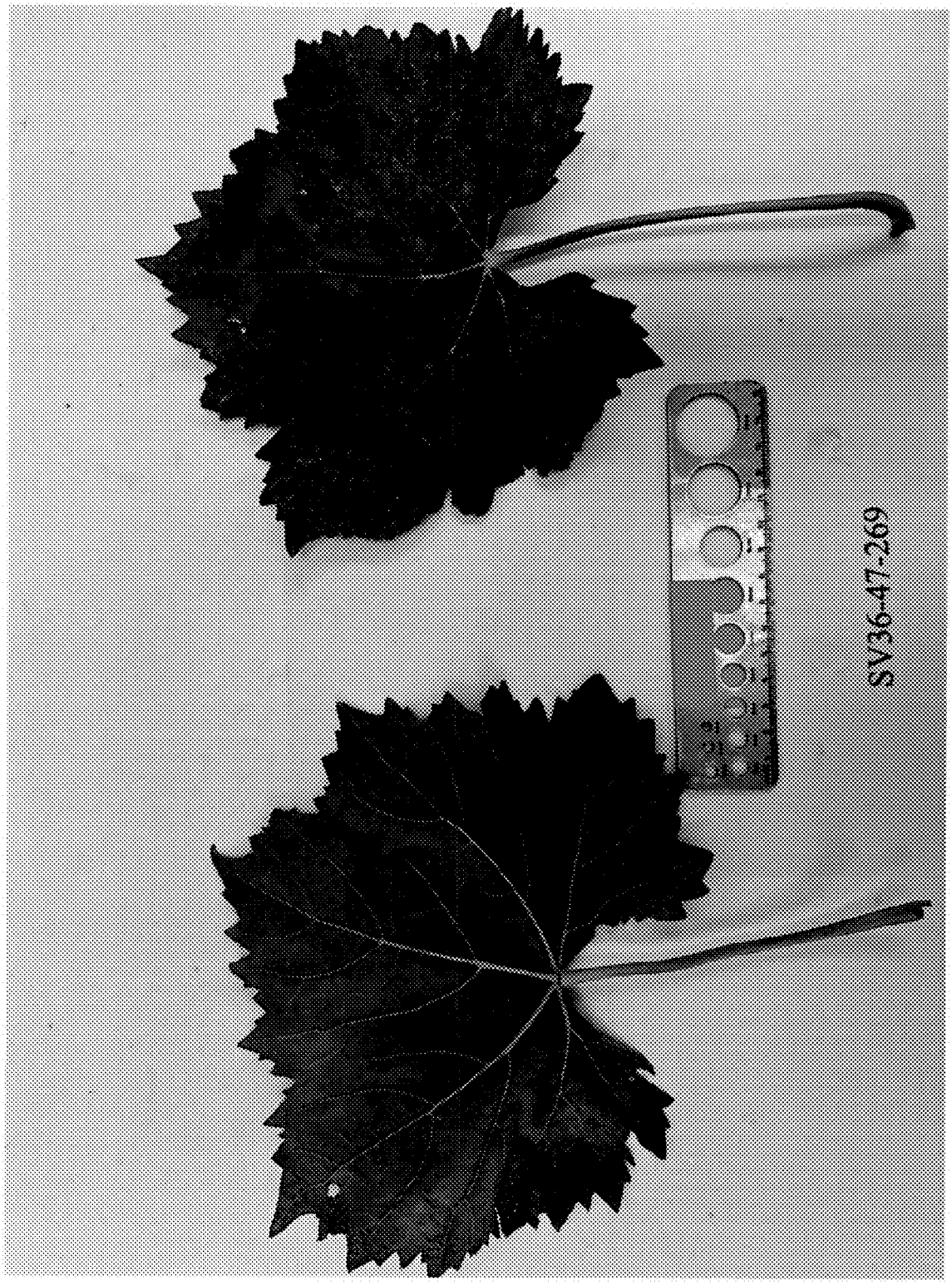
FIG. 3 Upper and lower surfaces of leaves.
Figure 4:
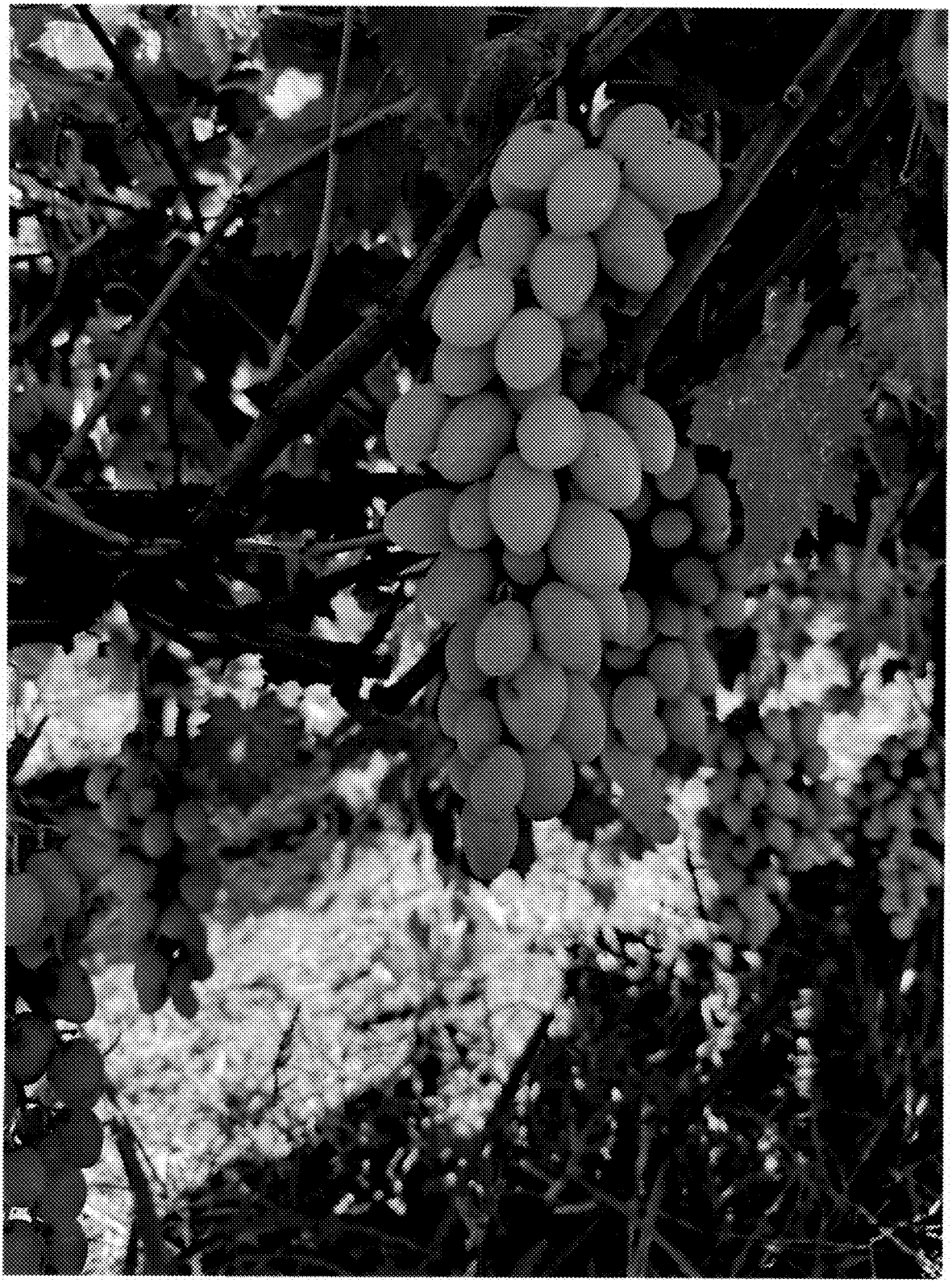
FIG. 4 Fruit on vine with no gibberellic acid application.
Figure 5:
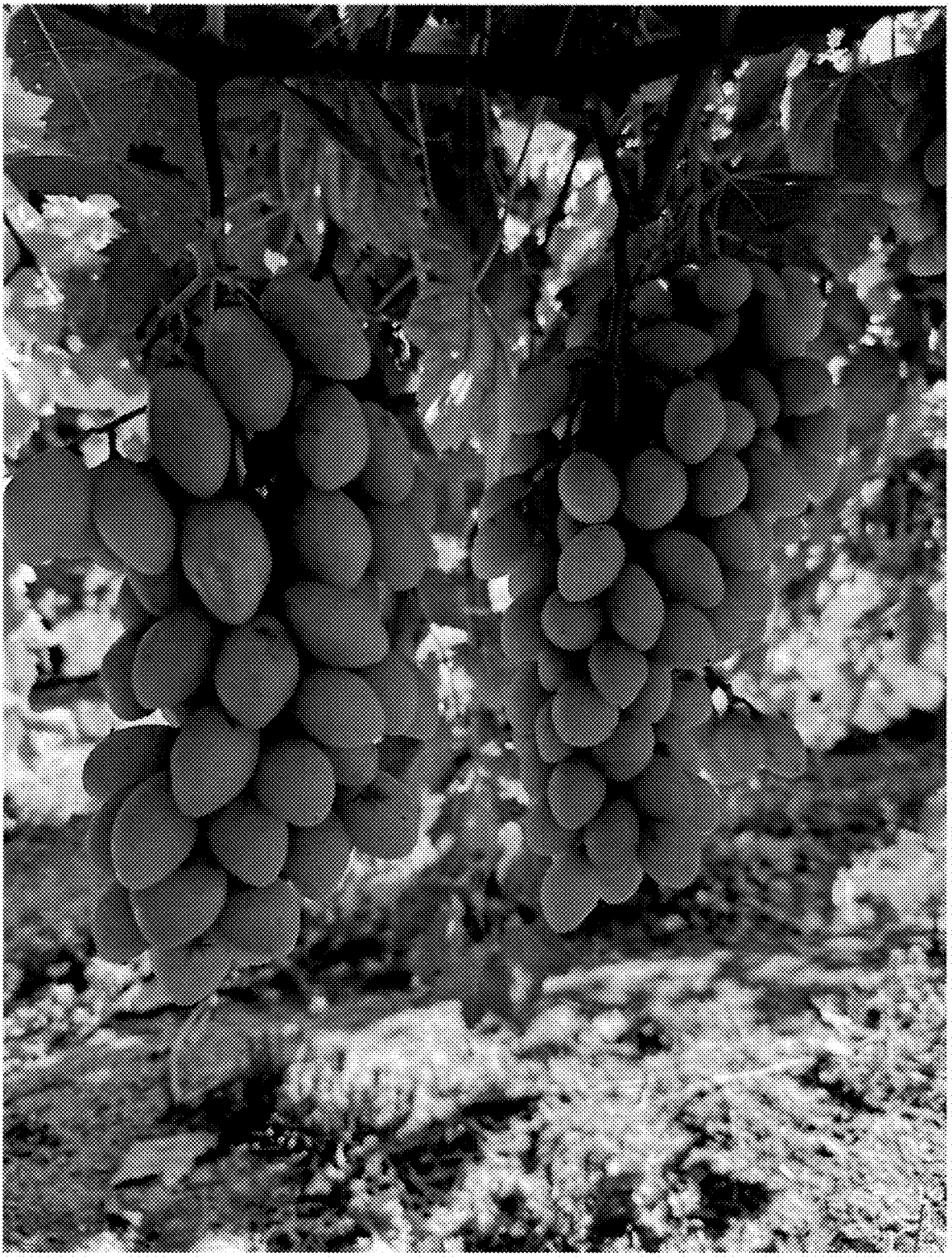
FIG. 5 Fruit on vine which was treated with gibberellic acid and trunk girdling.
Figure 6:
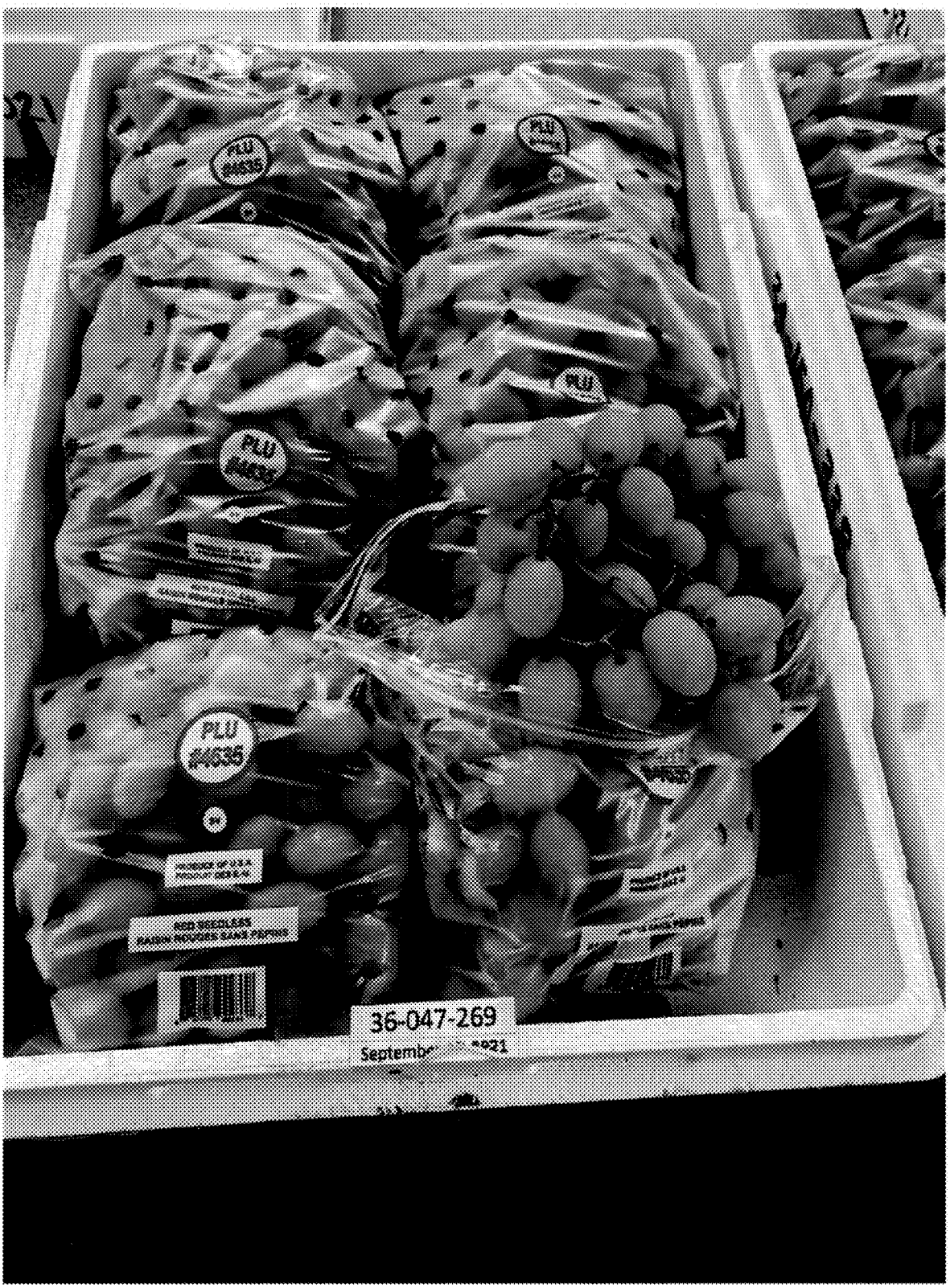
FIG. 6 Box of harvested fruit.

The following detailed description sets forth the distinctive characteristics of 'SV36-47-269'. Descriptions of the new invention apply to vines of 'SV36-47-269' grown on 'Freedom' rootstock at a density of 1,537 vines per hectare grown near McFarland, California in 2023. These vines were observed in the immediate year following planting and in the third year of full production having been planted in 2019. These descriptions are believed to apply generally to the new variety grown under similar circumstances elsewhere. Variation due to soil and climatic conditions in other locations may be seen. References to color correspond to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.

*Botanical name*.—*Vitis vinifera*.

*Variety name*.—'SV36-47-269'.

Plant:

*Vigor*.—Vines spur-pruned and shoot thinned to 32 shoots average 249.56 cm cm of growth per cane.

*Density of foliage*.—Moderate.

*Productivity*.—High, up to 40,050 kg/ha.

*Hardiness*.—Observed to 0° C.

*Rootstock*.—'Freedom' (unpatented).

*Bud burst*.—Medium.

Trunk:

*Shape*.—Broadly elliptical.

*Straps*.—Long, split.

*Surface texture*.—Shaggy.

*Trunk circumference*.—25.4 cm.

*Inner bark color*.—RHS Greyed-orange group 174B.

*Outer bark color*.—RHS Grey group 201A.

Mature leaves:

*Average blade length*.—17.6 cm.

*Average blade width*.—21.1 cm.

*Size of blade*.—Large.

*Shape*.—Pentagonal.

*Number of lobes*.—5.

*Anthocyanin coloration of main veins on the upper side of the blade*.—Absent.

*Mature leaf profile*.—Cupped upwards around entire margin.

*Blistering* (*upper surface*).—Absent.

*Leaf blade tip*.—Curved upwards.

*Margins*.—Lobed, Serrated, Undulating.

*Apex*.—Broadly acuminate.

*Bases*.—Sagittate.

*Thickness*.—Medium.

*Undulation of blade between main and lateral veins*.—Slight.

*Shape of teeth*.—Both sides straight (rectilinear).

*Length of teeth*.—9.6 mm.

*Width of teeth*.—11.4 mm.

*Ratio length/width of teeth*.—*About* 9.11.

*General shape of petiole sinus*.—Half open.

*Tooth at petiole sinus*.—Absent.

*Petiole sinus limited by veins*.—Absent.

*Shape of upper lateral sinus*.—Open.

*Prostrate hairs between veins* (*lower surface*).—Low density/sparse.

*Erect hairs between veins* (*lower surface*).—High density.

*Prostrate hairs on main veins* (*lower surface*).—Absent.

*Density of erect hairs on main veins* (*lower surface*) .—Absent.

*Prostrate hairs on main veins* (*upper surface*).—Low density/sparse.

*Upper surface*.—Summer color: Yellow-green group 147B. Surface texture: Smooth. Surface appearance: Dull. Goffering of blade: Absent.

*Lower surface*.—Summer color: Yellow-green group 146B. Anthocyanin coloration of main veins on lower leaf surface: Absent. Anthocyanin coloration on laterals: Absent. Glossiness: Low. Pubescence: Absent. Surface texture: Rough. Surface appearance: Dull.

*Petiole*.—Length: 16.6 cm. Length of petiole compared to middle vein: About equal. Density of prostrate hairs: Absent. Density of erect hairs: Absent. Shape of base of petiole sinus: Sagittate. Color: In shade: RHS Yellow-green group 144C. In sun: RHS Yellow-green group 144B.

Tendrils:

*Number & pattern*.—Bifurcated and trifurcated; Present every node after $6^{th}$.

*Length*.—25.5 cm.

*Diameter*.—3.2 mm.

*Texture*.—Smooth.

*Color*.—RHS Yellow-green group 144C.

Growing tips (young shoot):

*Pubescence*.—Abundant, prostrate.

*Color*.—RHS Yellow-green group 144B.

*Anthocyanins*.—Absent.

*Shape*.—Rounded.

*Apex*.—Fully Open.

*Shoot attitude*.—Semi-erect.

Green summer shoots:

*Internode color upper surface*.—RHS Yellow-green group 148A.

*Internode color lower surface*.—RHS Yellow-green group 144A.

*Node color upper surface*.—RHS Yellow-green group 148A.

*Node color lower surface*.—RHS Yellow-green group 145A.

*Density of erect hairs on internodes*.—Absent.

Woody shoot:

*Canes*.—Shape: Elliptic. Internode length: 10.6 cm. Width at node: 14 mm. Surface: Smooth. Main color: RHS Greyed orange 165B.

*Laterals*.—Shape: Elliptic. Number: 1-2. Length: 21.4 cm. Diameter: 4.8 mm. Internode length: 3.7 cm. Color: RHS Yellow-green group 144C.

*Buds*.—Shape: Rounded. Length: 4.8 mm. Width: 3.3 mm. Height: 3.1 mm. Color: RHS Greyed orange 166A.

Flowers:

*Flower sex*.—Perfect.

*Position of first flowering nodes*.—3rd-4$^{th}$.

*Number of inflorescences per shoot*.—2.

*Flower cluster width*.—4.4 cm.

*Flower cluster length*.—28.2 cm.

*Cluster stem color*.—RHS Yellow-Green group 145A.

*Calyptra color*.—RHS yellow-green group 144A.

*Ovary length*.—2.0 mm.

*Ovary width*.—1.7 mm.

*Ovary color*.—RHS yellow-green group 144A.

*Filament length*.—2.4 mm.

*Filament color*.—Translucent, absence of pigmentation.

*Anther length*.—0.8 mm.

*Anther color*.—RHS greyed-orange group N167B.

*Date of full bloom*.—May 6, 2024.

Fruit:

*Ripening period*.—Late season, McFarland, California.

*Date of ripening*.—Sep. 8, 2022, McFarland, California.

*Use*.—Fresh market.

*Keeping quality*.—Very good.

*Shipping quality*.—Good.

*Solids-sugar*.—High, about 22 brix at full maturity.

*Titratable acidity*.—0.45 g/liter.

*ph*.—3.79.

*Bunch*.—Size: Medium. Length (peduncle excluded): About 21.8 cm. Width: About 14.6 cm. Weight: Natural, without gibberellic acid treatment: 743 g. With gibberellic acid treatment: 627.5 g. Density: Loose but well-filled. Number of berries: 81.3. Form: Conical.

*Peduncle*.—Length: About 7.1 cm. Lignification: 4 cm of peduncle. Color: RHS yellow-green group 144A.

*Berry*.—Size: Large. Uniformity of size: Uniform. Weight. Natural, without gibberellic acid treatment: 7.3 g. With gibberellic acid treatment: 9.2 g. Shape: Natural, without gibberellic acid treatment: Ovate. With gibberellic acid treatment: Ovate. Presence of seeds: Natural berries produce two to three semi-lignified traces about 3 mm in length. Berries from vines treated with gibberellic acid produce very small, soft traces less than 1 mm in length. Cross section: Circular. Dimensions: Longitudinal axis: 3.1 cm at base. Horizontal axis: About 2.3 cm. Skin color (without bloom): RHS yellow-green group N144A. Coloration of flesh: Translucent; RHS yellow-green group 150B. Juiciness of flesh: Juicy. Berry firmness: Very crisp. Particular flavor: Neutral, muscat. Bloom (cuticular wax): Heavy. Pedicel length: 1.1 cm. Berry separation from pedicel: With difficulty.

*Skin*.—Thickness: Medium. Texture: Very crisp. Reticulation: Absent. Roughness: Absent. Tenacity: Tenacious to flesh. Tendency to crack: Resistant.

Ripening disease and insect resistance: No particular resistance or susceptibility has been observed. Normal disease control practices can be used.

Having thus described and illustrated our new variety of grapevine, I claim:

1. A new and distinct variety of grapevine plant named 'SV36-47-269', substantially as illustrated and described herein.

* * * * *